(12) United States Patent
Dutta et al.

(10) Patent No.: US 11,517,209 B2
(45) Date of Patent: Dec. 6, 2022

(54) PRESSURE SENSING GUIDEWIRE ASSEMBLIES AND SYSTEMS

(71) Applicant: Pathways Medical Corporation, Santa Clara, CA (US)

(72) Inventors: Goutam Dutta, Bangalore (IN); Nitin Patil, Santa Clara, CA (US)

(73) Assignee: PATHWAYS MEDICAL CORPORATION, Santa Clara, CA (US)

( * ) Notice: Subject to any disclaimer, the term of this patent is extended or adjusted under 35 U.S.C. 154(b) by 82 days.

(21) Appl. No.: 16/243,521

(22) Filed: Jan. 9, 2019

(65) Prior Publication Data

US 2019/0183355 A1 Jun. 20, 2019

Related U.S. Application Data

(63) Continuation of application No. PCT/US2017/042545, filed on Jul. 18, 2017.
(Continued)

(51) Int. Cl.
*A61B 5/0215* (2006.01)
*A61B 5/00* (2006.01)
(Continued)

(52) U.S. Cl.
CPC ........ *A61B 5/0215* (2013.01); *A61B 5/02158* (2013.01); *A61B 5/6851* (2013.01); *A61B 5/026* (2013.01); *A61B 5/02007* (2013.01)

(58) Field of Classification Search
CPC ...... A61B 2562/0247; A61B 2562/043; A61B 5/0004; A61B 5/002; A61B 5/02007;
(Continued)

(56) References Cited

U.S. PATENT DOCUMENTS

2002/0173724 A1 11/2002 Dorando et al.
2002/0198459 A1 12/2002 Franco et al.
(Continued)

FOREIGN PATENT DOCUMENTS

WO WO 2015/054296 4/2015
WO WO 2015/150913 10/2015
WO WO 2018/017547 1/2018

OTHER PUBLICATIONS

Bideaux, A., Zimmermann, B., Hey, S., & Stork, W. (2015). Synchronization in wireless biomedical-sensor networks with Bluetooth Low Energy, Current Directions in Biomedical Engineering, 1(1), 73-76. doi: https://doi.org/10.1515/cdbme-2015-0019 (Year: 2015).*
(Continued)

*Primary Examiner* — Sean P Dougherty
*Assistant Examiner* — Alexander H Connor
(74) *Attorney, Agent, or Firm* — Oliff PLC

(57) ABSTRACT

Pressure sensing guidewire assemblies are described herein where the guidewire assembly may be comprised of an elongate guidewire body and multiple pressure sensors secured near or at a distal end of the guidewire body. The signals obtained from the guidewire connectors and aortic sensor modules may be synchronized to minimize signal acquisition delays. The signals may be further processed to equalize the pressure waveforms by shifting the connector waveform to align correctly with the aortic module waveform and improve output signals.

22 Claims, 8 Drawing Sheets

Related U.S. Application Data

(60) Provisional application No. 62/363,995, filed on Jul. 19, 2016.

(51) Int. Cl.
  *A61B 5/026* (2006.01)
  *A61B 5/02* (2006.01)

(58) Field of Classification Search
  CPC ... A61B 5/0215; A61B 5/02158; A61B 5/026; A61B 5/6851
  See application file for complete search history.

(56) References Cited

U.S. PATENT DOCUMENTS

| | | | |
|---|---|---|---|
| 2011/0071407 A1 | 3/2011 | Hubinette et al. | |
| 2012/0265522 A1* | 10/2012 | Fex | G10L 21/04 704/E11.001 |
| 2013/0046190 A1 | 2/2013 | Davies | |
| 2013/0109980 A1 | 5/2013 | Teo | |
| 2014/0276142 A1* | 9/2014 | Dorando | A61B 5/0215 600/486 |
| 2016/0006526 A1* | 1/2016 | Cho | H04J 3/0697 370/503 |
| 2016/0073885 A1* | 3/2016 | Adler | A61B 5/0066 600/427 |
| 2016/0166158 A1* | 6/2016 | McCaffrey | A61B 5/02028 600/485 |
| 2016/0228013 A1* | 8/2016 | Al-Jilaihawi | A61B 5/0215 |

OTHER PUBLICATIONS

Bideaux et al. "Synchronization in wireless biomedical-sensor networks with Bluetooth Low Energy," *Current Directions in Biomedical Engineering*, vol. 1, No. 1, pp. 73-77, Sep. 12, 2015.

* cited by examiner

PRESSURE SENSING GUIDEWIRE ASSEMBLIES AND SYSTEMS

CROSS-REFERENCE TO RELATED APPLICATIONS

This application is a continuation of PCT/US2017/042545 filed Jul. 18, 2017, which claims the benefit of priority to U.S. Prov. 62/363,995 filed Jul. 19, 2016, each of which is incorporated herein by reference in its entirety.

FIELD OF THE INVENTION

This invention relates generally to methods and devices for determining physiological parameters within a patient's body. More particularly, this invention relates to methods and devices for intravascularly determining pressure within a vessel or lumen within the patient's body.

BACKGROUND OF THE INVENTION

Revascularization of vessels having greater than 70% stenosis is supported by data confirming the efficacy of both percutaneous and surgical methods of revascularization to treat angina pectoris. However, this decision is not obvious when it comes to a decision to re-vascularize intermediate lesions, e.g., 30% to 70% stenosis. A functional assessment of the stenosis can help to guide such decision. Fractional Flow Reserve (FFR) which is a ratio of pressure distal to the stenosis at maximal hyperemia (maximum physiologic flow) to the aortic pressure (Ao) is a clinical parameter used to determine functional significance of a lesion. The FFR is a fractional value that indicates how much the flow of blood to the vasculature of the myocardium through the blood vessel is compromised due to the stenosis. A value close to 1 indicates very little compromise. Decreasing values indicate increasing of compromise. A threshold of ischemia exists for FFR that allows the discrimination of functionally significant lesions. A FFR of below 0.75 is almost always associated with inducible ischemia. The randomised FAME trial (NEJM, 2009) showed that FFR-guided coronary intervention resulted in a significant reduction in coronary events and improved survival compared to simple angiographically-guided intervention.

The Aortic pressure (Ao) is typically obtained by putting an additional equipment that is in series between the Aortic sensor and the hemodynamic monitoring system (e.g., QUENTINE System, Saint Jude Medical, St. Paul, Minn.) or by taking the output from the hemodynamic monitor. Both of these methods involve installing additional equipment in the catheterization laboratory which is cumbersome, expensive, requires service and maintenance and can be a barrier to adoption. Additionally, there are interoperability challenges as there are several different hemodynamic monitor equipment manufacturers (GE, Philips, Siemens, Toshiba, etc.) to be interfaced and tested to further increasing system complexity and cost of carrying additional adaptors and cables.

Accordingly, there is a need for intravascular pressure measurement system which eliminates the need for additional capital equipment installations. Proposed system and associated algorithms and methods describe a novel approach to an FFR system that eliminates extra hardware and streamlines workflow and user experience.

SUMMARY OF THE INVENTION

In order to eliminate capital equipment in the catheterization laboratory is to utilize a guidewire having two pressure sensors integrated along the length of the guidewire. One variation for constructing a dual pressure sensor guidewire may involve using an 8-wire conducting flat wire along with a specifically designed flex circuit on the second sensor that has eight traces. Yet another alternative is to utilize a disposable Ao sensor that is integrated with the requisite electronic circuitry to amplify and digitize the sensor output. This Ao output is then either connected directly to the guidewire connector via a wired connection or the output signal may be transmitted wirelessly to a remote processing unit (e.g., tablet, computer, etc.). A wireless connection between the guidewire connector, aortic sensor module and the processing unit (e.g. tablet, laptop, desktop computer, mobile device, etc.) is a configuration which may eliminate cables to keeps the area around the patient decongested.

In one variation, the guidewire sensing device may generally comprise a guidewire having an elongate body, a guidewire connector positioned at a proximal end of the body, an aortic sensor module positioned along the elongate body and distal to the connector, a processing unit located remotely from the guidewire and in wireless communication with the guidewire connector and aortic sensor module, and wherein the processing unit is configured to transmit timing information between the guidewire connector and the aortic senor module such that a sampling time of the guidewire connector and aortic sensor module is synchronized with one another.

In one variation for a method of measuring parameters with a guidewire, method may generally comprise providing a guidewire having an elongate body with a guidewire connector positioned at a proximal end of the body and an aortic sensor module positioned along the elongate body and distal to the connector, wirelessly transmitting timing information between a processing unit and the guidewire connector and aortic sensor module, wherein the processing unit is located remotely from the guidewire, and synchronizing a sampling time of the guidewire connector and aortic sensor module based on the timing information.

The remote processing unit may pair with one guidewire connector and one aortic sensor module at a time. Wireless configuration between the various modules comes with their own set of challenges. One of the challenges encountered is the timing synchronization between the guidewire connector and the aortic module. The timing synchronization helps to ensure accuracy of the FFR diagnostic. The timing synchronization can be achieved between the connector and the aortic module through repeated transmission of each other's timing information over the wireless link. Alternately, the timing synchronization can also be achieved between the individual devices (connector and aortic module) and the processing unit. The processing unit software then instructs the individual devices to start acquiring at similar time instances after adjusting their individual time biases. The latter method is particularly useful for configurations where the processing unit is the assigned master and the connector and aortic module are peripheral devices.

At the beginning of the protocol, the connection interval is reduced to its minimum possible value to ensure that the network delays are minimized. The processing unit software then proceeds to perform timing synchronization with one of the two devices (e.g. connector and aortic module).

The processing unit software starts the transaction by first noting its own local time and immediately querying for the remote time at the device end. The device on receipt of the query, responds back with its current time along with a cyclic redundancy check (CRC). The processing unit software notes its own time as soon as it receives the response from the device. It immediately sends another query to the device. The device on receipt of the second query again sends back its current time along with is CRC. A given iteration is aborted if any of the transactions fail.

Assuming that the time offset between the processing unit software and the device is $\Delta$, a local estimate ($\Delta_1$) computed at the processing unit end and remote estimate ($\Delta_2$) computed at the device end are generated and an average value of $\Delta_1$ and $\Delta_2$ measured over a statistically significant number of timing synchronization attempts are both measures of the time delay ($\Delta$) between processing unit software and the BLE device with a bias depending on the relative delays of transmit and receive paths of processing unit software and BLE device. These delays are small and may be ignored to the first order approximation.

A decent estimate of the time bias requires a statistically significant number of iterations. A random delay is inserted between two consecutive iteration loops. The delay value ranges between 0 to the updated connection interval. The introduction of random delays ensures a true uniform distribution of packet arrivals with respect to the BLE slot segment and provides an unbiased estimate of the relative bias. Iterations are considered to be complete if all the transactions of that iteration are successful. A particular iteration is aborted and ignored if a given transaction times out.

On the completion of the timing synchronization iterations with the connector and the aortic module, the processing unit software calculates the estimated time bias of the connector and the aortic module with respect to the internal clock of the tablet.

At the start of data acquisition, the processing unit software checks its own local time and adds a pre-determined fixed delay to it. It then estimates the acquisition start time (also referred to as strobe time) for each of the devices after adjusting their estimated time biases. The strobe time for each of these devices are sent to them, and they start their respective acquisitions only when their internal time crosses over the strobe time it has received from the tablet software. The addition of a fixed delay (significantly larger than wireless propagation delay) ensures that both devices would have received their commands to start acquisition before the lapse of the strobe time.

It may be noted that the intent of the timing synchronization is to synchronize the sampling time of the connector and aortic module. Since both devices employ similar firmware and is synchronized with very similar functionalities in processing unit software, both of them would also experience very similar biases in their estimate. Hence, in reality the biases introduced by the relative delays of transmit and receive paths of processing unit software and BLE devices become a common-mode bias and get cancelled out.

The equalization technique wherein the aortic sensor and the guidewire sensor measure the same pressure waveform provides another opportunity to perform timing synchronization using signal processing methods. Classically, the equalization technique corrects for the gain error of the guidewire sensor waveform (output of the connector) while treating the aortic sensor waveform as a reference. The bias error of the sensors is corrected during zeroing.

However, sensor biases tend to drift once the sensor is inserted from outside to inside the human body as this drift is largely caused by temperature variations. One variation of an equalization technique described herein not only addresses the gain error of the guidewire sensor but also addresses any residual post zeroing bias error due to bias drift as well as shifts in time axis due to inadequacy of timing synchronization.

The connector waveform is time shifted by an unknown amount and has a gain error and residual bias error. The two waveforms are initially correlated with the connector waveform shifted in time base. The correlation coefficients between the two waveforms are noted for different time base shifts and the best correlation coefficient provides the correct estimate of the amount of shift required for the connector waveform to align correctly with the aortic module waveform. Once aligned correctly, the gain error and residual bias estimate are easily obtained using standard statistical techniques.

The next challenge in using a wireless configuration for both sensor signals (distal pressure measured by guidewire and Aortic pressure measured by Ao module) is the frequency mismatch of the sampling clock of the guidewire connector and the aortic connector. A frequency mismatch of the sampling clocks between the two modules can lead to differences in the sampling time instances that would grow with time. One of the ways to control the effect of sampling frequency mismatch is to specify the tolerance of sampling clocks depending on the accuracy requirement of the measurement system and the maximum length of time the system shall be used without an equalization being done.

Another method includes using an accurate RTC clock on both the guidewire connector as well as the aortic module for timestamping the exact individual sampling instances and performing complex re-sampling techniques on one of them to match the sampling time of the other. The RTC counters of the individual modules may be synchronized accurately a priori using methods discussed herein.

Yet another method involves long equalization periods during which both the guidewire connector and the aortic module samples the same pulsatile aortic pressure. Frequency mismatches are estimated using complex signal processing techniques and compensated for. In practice, any one of the embodiments herein or, even a combination of these embodiments may be used for compensating frequency mismatch.

Wireless configurations might result in loss of data packets or, arrival of corrupt packets. Most protocols do support re-transmissions where a transaction is complete only after a receiver sends an acknowledgement and the same is received by the transmitter. The transmitter re-transmits old packets if it misses out on acknowledgement from the receiver. This might lead to delayed arrival of packets and wrong sequence of arrivals. The data sampled at individual modules are assigned sample identification numbers before transmission. The tablet on receiving the data packets from an individual module buffers them and re-arranges the packets in order of sample identification numbers.

One technique for guiding the user to perform equalization involves adjustment of the guidewire sensor measurements to match aortic sensor measurements when both of them measure the aortic pressure. Since both sensors measure the same signal during equalization, the two measurements should be very well correlated. In reality sensor measurements may get affected due to local disturbances near sensor diaphragm, leakage in guide catheter etc. that may result in imperfect match between signals. An algorithm continuously computing a correlation score between the two sensor measurements may be deployed which guides the user for performing equalization only when the correlation score is higher than a pre-defined threshold.

The user may be notified of this either through a message on a user interface screen or through a color coding scheme on the soft buttons meant for zeroing and equalization (e.g., the soft buttons turn green when the system finds a suitable duration to perform zeroing/equalization and red when the system does not find the duration suitable for the respective operations).

In a typical user interface for FFR applications, the user can be provided with either a soft menu option or a physical button to perform certain application specific tasks such as, e.g., zeroing, equalization, to start and stop recording of data and to toggle between an active data acquisition state to data analysis/data saving states. One of the methods to reduce the need of interaction with the processing and display unit (e.g. tablet, laptop, desktop computer, mobile device, etc.) is to design a context driven user interface that would allow the most likely state transitions with, e.g., a click of a single button. A possible location of the button is on the connector which can be handled by the physician. Other options for controlling the state transitions can be through, e.g., stand-alone wired or wireless joysticks/mouse, etc.

DETAILED DESCRIPTION OF THE INVENTION

The aortic pressure Ao is used to compute FFR and this is typically done by tapping the Aortic pressure signal output either from the Aortic pressure sensor in series with the hemodynamic monitor or by using the output on the hemodynamic system. There are several ways of eliminating the need for this additional capital equipment in the catheterization laboratory. One way to accomplish this is to have a second pressure sensor positioned about, e.g., 15 to 20 cm, proximal to the distal pressure sensor as this eliminates the need to measure Ao through an external pressure sensor altogether. However, mounting a second sensor on a guidewire without affecting its performance is challenging.

Figure 1:
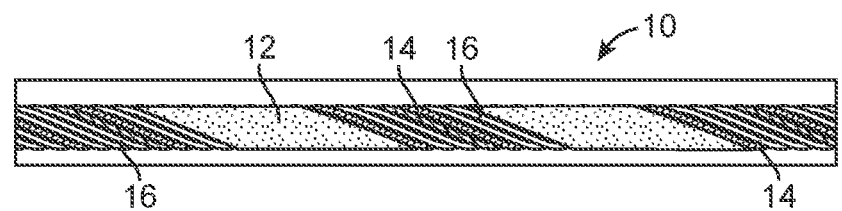
FIG. 1 shows an example of one variation of a guidewire assembly in which a guidewire core shaft was constructed with at least one helical groove defined over at least a length of the guidewire core shaft.

One variation for constructing a dual pressure sensor guidewire may involve using an 8-wire conducting flat wire along with a specifically designed flex circuit on the second sensor that has eight traces. FIG. 1 shows an example of one variation of a guidewire assembly 10 in which a guidewire core shaft 12 was constructed with at least one helical groove 14 defined over at least a length of the guidewire core shaft 12 to where the pressure sensors are positioned along the core shaft 12. This helical groove 14 has a width sized to accommodate 8-conducting cables 16 aligned adjacent to one another that are used to route conducting signals from two different pressure sensors.

Figure 2A:
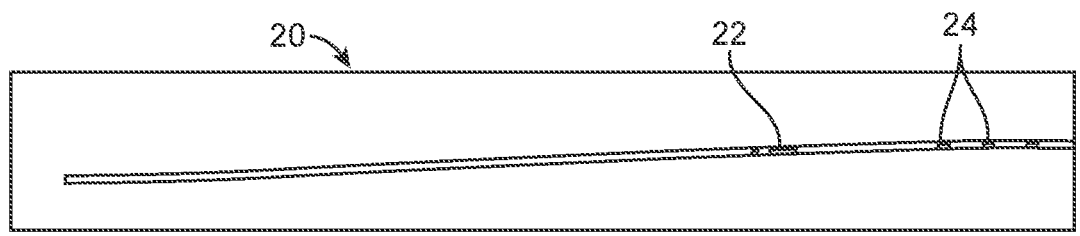
FIG. 2A shows a side view of a full guidewire using 8-conducting cables constructed to demonstrate feasibility of this concept.
Figure 2B:
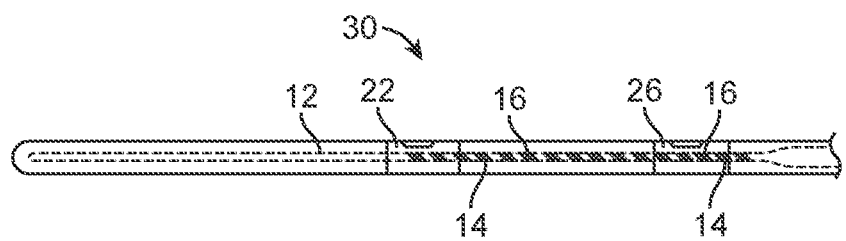
FIG. 2B shows a side view of one variation of how a first pressure sensor and a second pressure sensor may be incorporated along a length of the single guidewire.

FIG. 2A shows a side view of a full guidewire 20 (e.g., 0.014 in) using 8-conducting cables 16 constructed to demonstrate feasibility of this concept. This guidewire 20 incorporated a pressure sensor 22 and four electric sensors 24 at the distal end of the guidewire 20. Similarly, FIG. 2B shows a side view of one variation of how a first pressure sensor 22 and a second pressure sensor 26 may be incorporated along a length of the single guidewire 30 and how the helical groove 14 may be defined along the length of the guidewire core shaft 12 between the pressure sensors 22, 26. The 8-conducting cables 16 may be positioned within the length of the helical groove 14 for electrical connection to both of the pressure sensors 22, 26.

Alternatively in other variations, conductive traces may be printed on a polymeric substrate placed over a length of the guidewire core rather than using the cables 16 positioned within the helical groove 14.

Figure 2C:
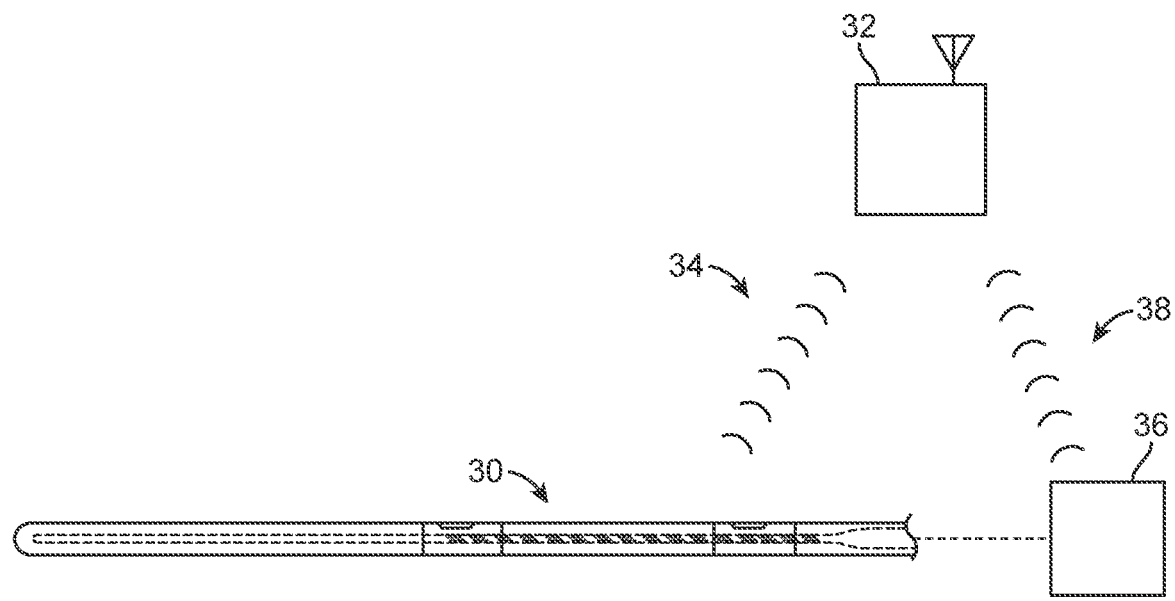
FIG. 2C shows one variation where the remote processing unit is wirelessly in communication with the aortic sensor module and guidewire connector.
Figure 2D:
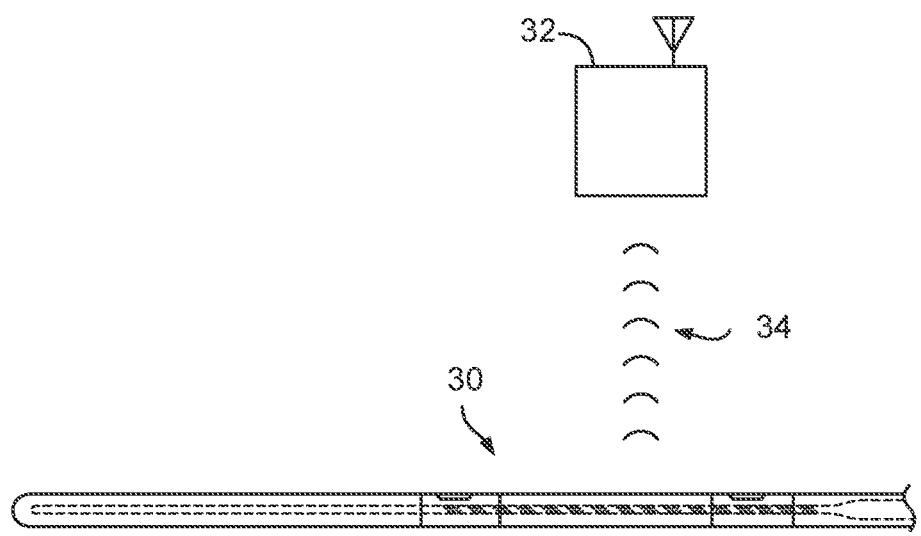
FIG. 2D shows the Ao output signal transmitted wirelessly to a remote processing unit.

Yet another alternative is to utilize a disposable Ao sensor that is integrated with the requisite electronic circuitry to amplify and digitize the sensor output. This Ao output is then either connected directly to the guidewire connector via a wired connection or the output signal may be transmitted wirelessly to a remote processing unit 32 (e.g., tablet, laptop, desktop computer, mobile device, etc.) as shown in FIG. 2D. FIG. 2C illustrates another example of a wireless connection 34 between the guidewire connector 36, aortic sensor module 30 and the processing unit 32 is a configuration which may eliminate cables to keeps the area around the patient decongested.

In such a mode of implementation, the remote processing unit 32 may pair with one guidewire connector 36 and one aortic sensor module 30 at a time. The pairing may be accomplished through an identification key that is unique for a guidewire connector and an aortic sensor module. Furthermore, the guidewire connectors and aortic sensor modules may follow a different series of unique identification keys that enables the remote processing unit to identify the group correctly.

Wireless configuration between the various modules comes with their own set of challenges. One of the challenges encountered is the timing synchronization between the guidewire connector and the aortic module. The timing synchronization helps to ensure accuracy of the FFR diagnostic. The timing synchronization can be achieved between the connector and the aortic module through repeated transmission of each other's timing information over the wireless link. Alternately, the timing synchronization can also be achieved between the individual devices (connector and aortic module) and the processing unit. The processing unit software then instructs the individual devices to start acquiring at similar time instances after adjusting their individual time biases. The latter method is particularly useful for configurations where the processing unit is the assigned master and the connector and aortic module are peripheral devices.

A description is provided for timing synchronization achieved between the processing unit and the individual devices linked over, e.g., a low energy BLUETOOTH (Bluetooth SIG, Inc., Kirkland, Wash.) link (BLE). Similar methods with minor adaptations can be employed for different wireless links and protocols (e.g. Zigbee, WiFi, etc).

Figure 3:
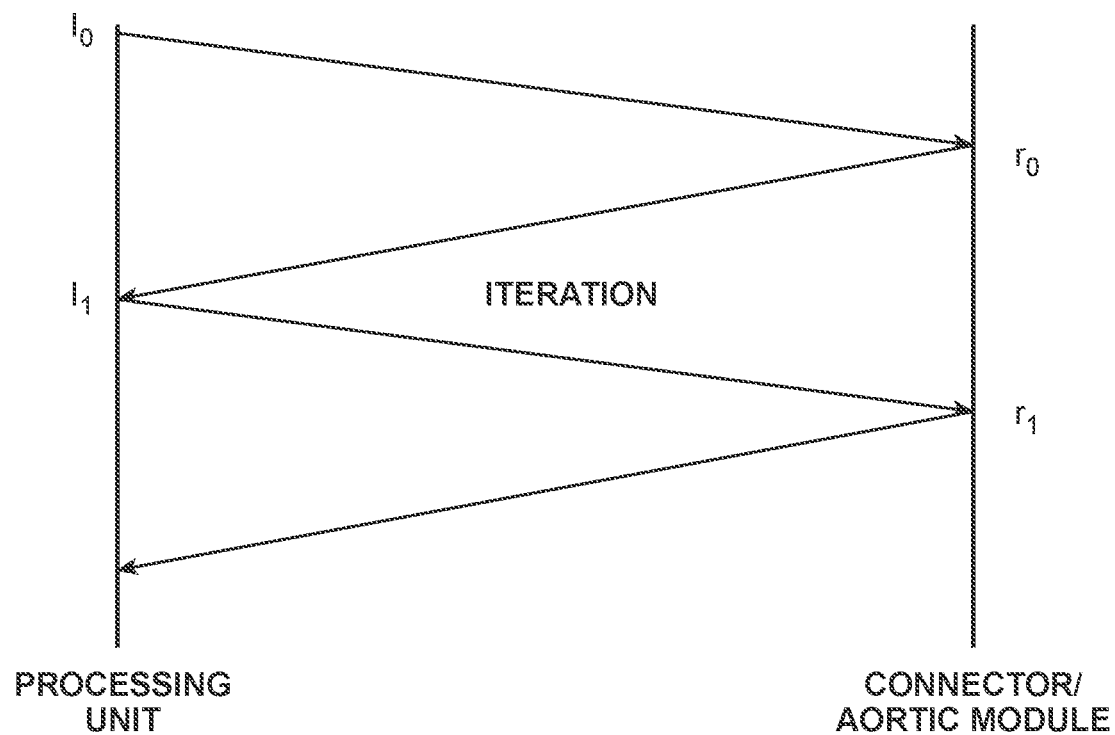
FIG. 3 diagrammatically shows an example of how a connection interval may be reduced to its minimum possible value to ensure that the network delays are minimized.

At the beginning of the protocol, as illustrated diagrammatically in FIG. 3, the connection interval (CI) is reduced to its minimum possible value to ensure that the network delays are minimized. The processing unit software then proceeds to perform timing synchronization with one of the two devices (e.g. connector and aortic module).

The processing unit software starts the transaction by first noting its own local time ($l_0$) and immediately querying for the remote time at the device end. The device on receipt of the query, responds back with its current time ($r_0$) along with a cyclic redundancy check (CRC). The processing unit software notes its own time ($l_1$) as soon as it receives the response from the device. It immediately sends another query to the device. The device on receipt of the second query again sends back its current time ($r_1$) along with is CRC. A given iteration is aborted if any of the transactions fail.

Assuming that the time offset between the processing unit software and the device is $\Delta$, the relationship between $l_0$, $l_1$, $r_0$ and $r_1$ can be written as:

$$r_0 = l_0 + \Delta + \tau_{AT} + \tau_{BR} + \tau_{s1} \quad (1)$$

$$l_1 = r_0 - \Delta + \tau_{BT} + \tau_{AR} + \tau_{s2} \quad (2)$$

$$r_1 = l_1 + \Delta + \tau_{AT} + \tau_{BR} + \tau_{s3} \quad (3)$$

where,
$\tau_{AT}$=Transmit path delay in processing unit software
$\tau_{AR}$=Receive path delay in processing unit software
$\tau_{BT}$=Transmit path delay in BLE device
$\tau_{BR}$=Receive path delay in BLE device
$\tau_s$=Slot delays for BLE packet (uniform distribution between 0 to Connection interval (7.5 ms)

The local estimate ($\Delta_1$) computed at the processing end and remote estimate ($\Delta_2$) computed at the device end is given by:

$$\Delta_1 = r_0 - \frac{l_0 + l_1}{2} = \Delta + (\varphi_A - \varphi_B) + \delta_{slot} \quad (4)$$

$$\Delta_2 = \frac{r_0 + r_1}{2} - l_1 = \Delta + (\varphi_A - \varphi_B) + \delta_{slot} \quad (5)$$

where,
$\varphi_A$=Difference between transmit path and receive path delays in processing unit software
$\varphi_B$=Difference between transmit path and receive path delays in BLE device
$\delta_{slot}$=Difference between two slot delays; a triangular distribution between −CI to +CI with mean of 0.

An average value of $\Delta_1$ and $\Delta_2$ measured over a statistically significant number of timing synchronization attempts are both measures of the time delay ($\Delta$) between processing unit software and the BLE device with a bias depending on the relative delays of transmit and receive paths of processing unit software and BLE device. These delays are small and may be ignored to the first order approximation.

A decent estimate of the time bias requires a statistically significant number of iterations, e.g., at least 30 or more. A random delay is inserted between two consecutive iteration loops. The delay value is between 0 to the updated connection interval. The introduction of random delays ensures a true uniform distribution of packet arrivals with respect to the BLE slot segment and provides an unbiased estimate of the relative bias. Iterations are considered to be complete if all the transactions (as shown in FIG. 3) of that iteration are successful. A particular iteration is aborted and ignored if a given transaction times out.

The mean value of $\overline{\Delta_1}$ and $\overline{\Delta_2}$ can also be used to compute the time delay:

$$\Delta = \frac{\overline{\Delta_1} + \overline{\Delta_2}}{2} \quad (6)$$

The difference between two mean values provides the goodness of the estimate.

$$\overline{\Delta_1} - \overline{\Delta_2} \leq \varepsilon, \quad (7)$$

where, $\varepsilon$ is a pre-determined threshold.

On the completion of the timing synchronization iterations with the connector and the aortic module, the processing unit software calculates the estimated time bias (using equation 6) of the connector and the aortic module with respect to the internal clock of the tablet.

At the start of data acquisition, the processing unit software checks its own local time and adds a pre-determined fixed delay to it. It then estimates the acquisition start time (also referred to as strobe time) for each of the devices after adjusting their estimated time biases (equations 8 and 9). The strobe time for each of these devices are sent to them, and they start their respective acquisitions only when their internal time crosses over the strobe time it has received from the tablet software. The addition of a fixed delay (significantly larger than wireless propagation delay) ensures that both devices would have received their commands to start acquisition before the lapse of the strobe time.

$$T_S^{Conn} = T_0 + T_D - \tau_{bias}^{Conn} \quad (8)$$

$$T_S^{Aortic} = T_0 + T_D - \tau_{bias}^{Aortic} \quad (9)$$

where,
$T_0$=Local time of the tablet during initiation of acquisition
$T_D$=Fixed time bias added by the tablet
$\tau_{bias}^{Conn}$=Estimated time bias of the connector with respect to the tablet
$\tau_{bias}^{Aortic}$=Estimated time bias of the aortic module with respect to the tablet
$T_S^{Conn}$=Time at which the connector would start its acquisition
$T_S^{Aortic}$=Time at which the aortic module would start its acquisition It may be noted that the intent of the timing synchronization is to synchronize the sampling time of the connector and aortic module. Since both devices employ similar firmware and is synchronized with very similar functionalities in processing unit software, both of them would also experience very similar biases in their estimate. Hence, in reality the biases introduced by the relative delays of transmit and receive paths of processing unit software and BLE devices become a common-mode bias and get cancelled out.

Figure 4:
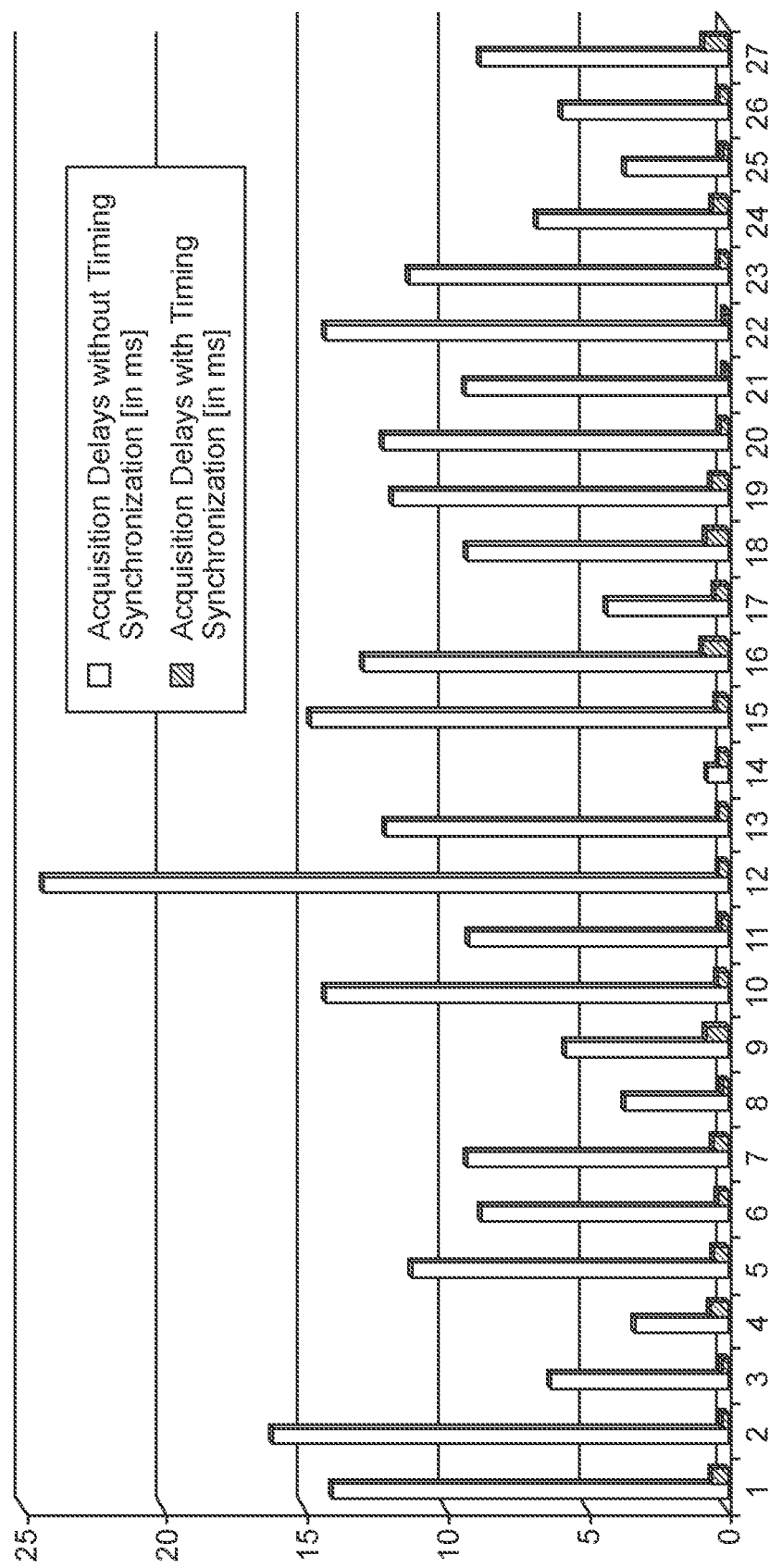
FIG. 4 shows a graph of the differences in acquisition delays with and without timing synchronization.

Measurements were done with 27 different attempts of timing synchronization each with 100 iterations, as illustrated in the graph of FIG. 4. As a comparison point, measurements were also made on the relative arrivals of the acquisition command to these devices. In absence of timing synchronization, the arrival of the acquisition command would initiate the acquisition process.

The result shows a significant improvement of timing alignment between the sampling instances of the connector and the aortic module. The mean differential delay of arrival of the acquisition command to the connector and the aortic module is about 10 ms with a standard deviation of 5 ms. The delay consists of the BLE physical layer delay as well as differential delays in the tablet software layers and the firmware layers of the connector and the aortic module.

With timing synchronization the mean differential delay of sampling reduces to about 400 µs with a standard deviation of 250 µs.

The equalization technique wherein the aortic sensor and the guidewire sensor measure the same pressure waveform provides another opportunity to perform timing synchronization using signal processing methods. Classically, the equalization technique corrects for the gain error of the guidewire sensor waveform (output of the connector) while treating the aortic sensor waveform as a reference. The bias error of the sensors is corrected during zeroing.

However, sensor biases tend to drift once the sensor is inserted from outside to inside the human body as this drift is largely caused by temperature variations. One variation of an equalization technique described herein not only addresses the gain error of the guidewire sensor but also addresses any residual post zeroing bias error due to bias drift as well as shifts in time axis due to inadequacy of timing synchronization.

Figure 5:
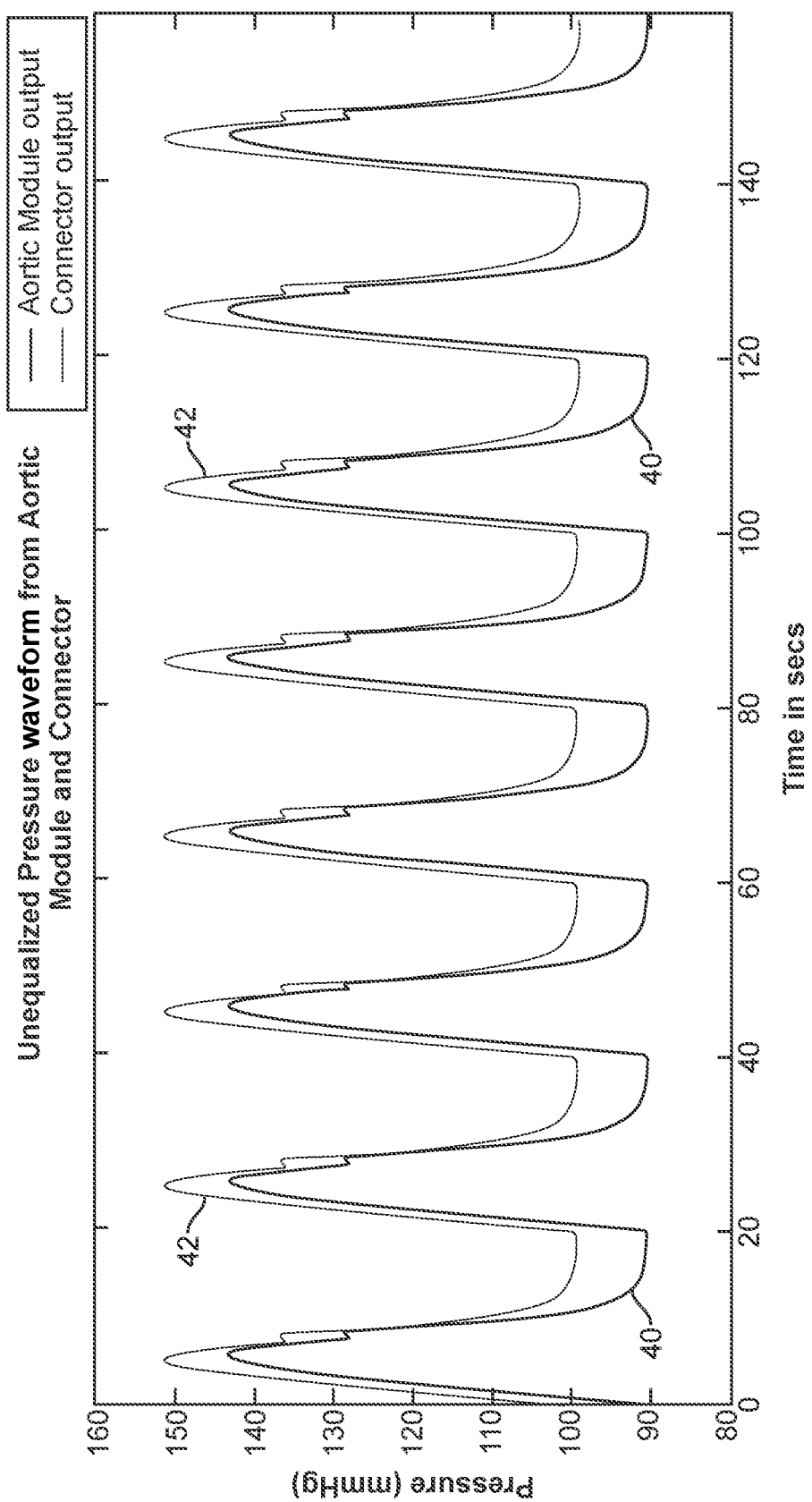
FIG. 5 shows an example of un-equalized pressure waveforms from the aortic module and connector.

FIG. 5 shows an example of un-equalized pressure waveforms from aortic module 40 and connector 42. The connector waveform is time shifted by an unknown amount and has a gain error and residual bias error. The two waveforms are initially correlated with the connector waveform shifted in time base. The correlation coefficients between the two waveforms are noted for different time base shifts and the best correlation coefficient provides the correct estimate of the amount of shift required for the connector waveform to align correctly with the aortic module waveform.

Figure 6:
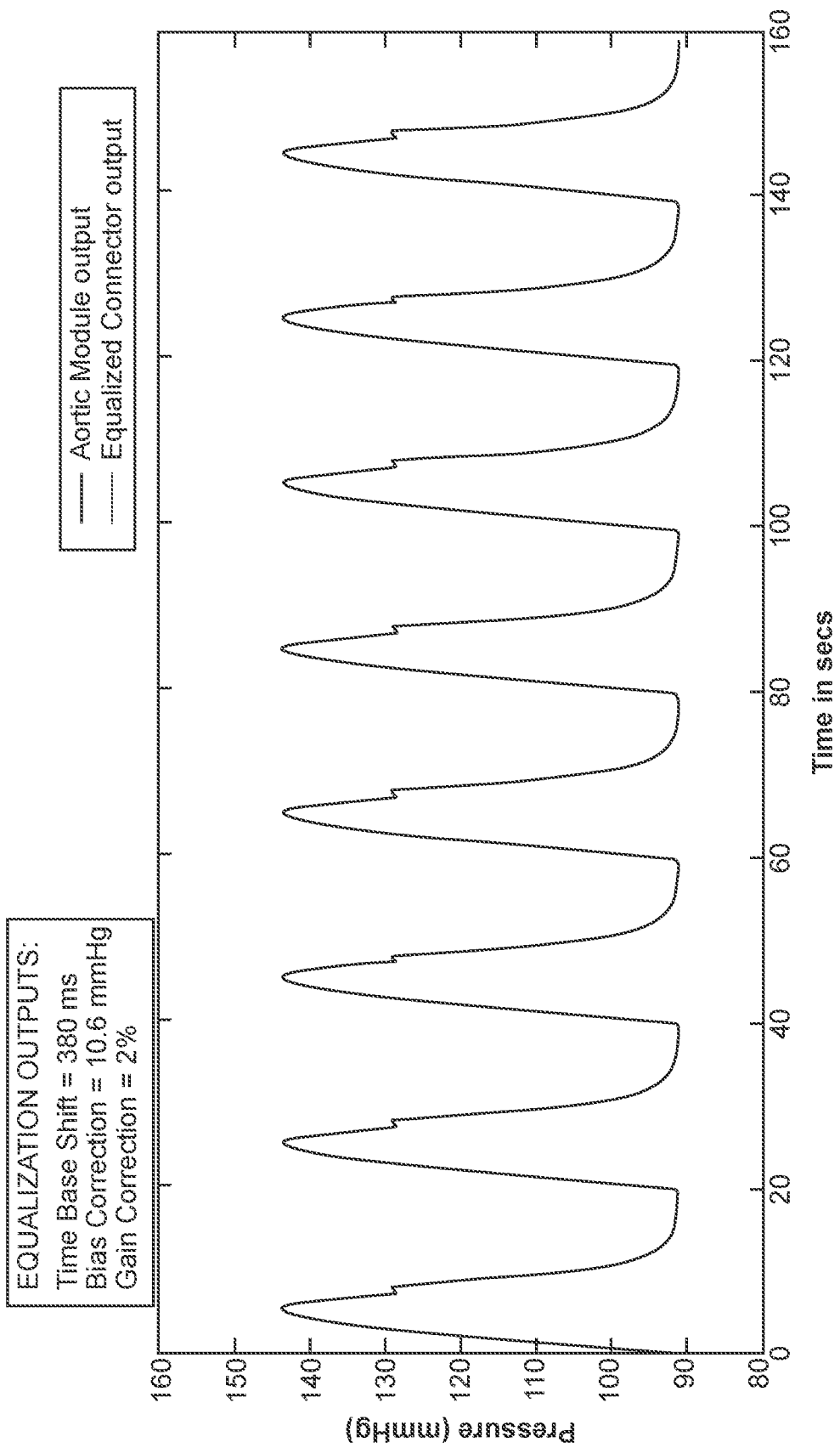
FIG. 6 shows the waveform of the aortic module and the equalized waveform from the connector.

Once aligned correctly, the gain error and residual bias estimate are easily obtained using standard statistical techniques:

$$m = \frac{(\overline{xy} - \overline{x}\,\overline{y})}{(\overline{x^2} - \overline{x}^2)} \quad (10)$$

$$c = \overline{y} - m\overline{x} \quad (11)$$

where,
x=the aortic module waveform
y=the time shifted connector waveform
m=the slope of y with respect to x and (m−1) is the gain error
c=the residual bias error FIG. 6 shows the waveform of the aortic module and the equalized waveform from the connector (the plots are overlaid on top of each other and cannot be distinguished). The equalization scheme provides the time shift of the connector waveform, gain correction and bias correction. Since the equalization works on sampled waveform, the accuracy of timing accuracy would be at best limited to accuracy of $$\left[ -\frac{T_S}{2} \text{ to } \frac{T_S}{2} \right]$$

where $T_S$ is the sampling frequency.

The next challenge in using a wireless configuration for both sensor signals (distal pressure measured by guidewire and Aortic pressure measured by Ao module) is the frequency mismatch of the sampling clock of the guidewire connector and the aortic connector. A frequency mismatch of the sampling clocks between the two modules can lead to differences in the sampling time instances that would grow with time. One of the ways to control the effect of sampling frequency mismatch is to specify the tolerance of sampling clocks depending on the accuracy requirement of the measurement system and the maximum length of time the system shall be used without an equalization being done.

Another method includes using an accurate real-time clock (RTC) on both the guidewire connector as well as the aortic module for timestamping the exact individual sampling instances and performing complex re-sampling techniques on one of them to match the sampling time of the other. The RTC counters of the individual modules may be synchronized accurately a priori using methods discussed herein.

Yet another method involves long equalization periods during which both the guidewire connector and the aortic module samples the same pulsatile aortic pressure. Frequency mismatches are estimated using complex signal processing techniques and compensated for. In practice, any one of the embodiments herein or, even a combination of these embodiments may be used for compensating frequency mismatch.

Wireless configurations might result in loss of data packets or, arrival of corrupt packets. Most protocols do support re-transmissions where a transaction is complete only after a receiver sends an acknowledgement and the same is received by the transmitter. The transmitter re-transmits old packets if it misses out on acknowledgement from the receiver. This might lead to delayed arrival of packets and wrong sequence of arrivals. The data sampled at individual modules are assigned sample identification numbers before transmission. The tablet on receiving the data packets from an individual module buffers them and re-arranges the packets in order of sample identification numbers.

For low power implementation of FFR on small disposable electronics, it is desirable to keep the electronics simple, low power, and low cost. These requirements mandate the use of lower resolution electronics. Miniaturized MEMS sensors are often subject to high variation of bias. In fact bias variations of MEMS sensor compel the electronics to accommodate for high dynamic ranges of signal. In some implementations, the sensors may measure incident pressure with respect to atmospheric pressure. In other implementations, sensors measure pressure with respect to zero pressure (close to absolute vacuum). In the later implementation, relative pressure measurements (with respect to atmospheric pressure) are also affected by local variations of atmospheric pressures.

Aside from synchronization, the system may also include zeroing which involves estimation of the mean signal value when the sensor is measuring atmospheric pressure followed by cancellation of the same. It is desirable to ensure that variability of the signal is minimized prior to zeroing to ensure an accurate estimate of the mean signal value. Variability of signals can be caused by multiple effects such as system noise, physical movements of the sensors, or formation of local air bubbles in the proximity of sensors flushed with saline. An algorithm by the processing unit 32 that continuously runs in the background checks for signal variability and advises the user to zero only when the signal variability is below a pre-defined threshold has been deployed. In another embodiment, the user may proceed with zeroing, with the background algorithm allowing the zeroing to happen only when conditions are suitable for zeroing.

One technique for guiding the user to perform equalization involves adjustment of the guidewire sensor measurements to match aortic sensor measurements when both of them measure the aortic pressure. Since both sensors measure the same signal during equalization, the two measurements should be very well correlated. In reality sensor measurements may get affected due to local disturbances near sensor diaphragm, leakage in guide catheter etc. that may result in imperfect match between signals. An algorithm continuously computing a correlation score between the two sensor measurements may be deployed which guides the user for performing equalization only when the correlation score is higher than a pre-defined threshold.

The user may be notified of this either through a message on a user interface screen or through a color coding scheme on the soft buttons meant for zeroing and equalization (e.g., the soft buttons turn green when the system finds a suitable duration to perform zeroing/equalization and red when the system does not find the duration suitable for the respective operations).

In a typical user interface for FFR applications, the user can be provided with either a soft menu option or a physical button to perform certain application specific tasks such as, e.g., zeroing, equalization, to start and stop recording of data and to toggle between an active data acquisition state to data analysis/data saving states. One of the methods to reduce the need of interaction with the processing and display unit (e.g. tablet, laptop, desktop computer, mobile device, etc.) is to design a context driven user interface that would allow the most likely state transitions with, e.g., a click of a single button. A possible location of the button is on the connector which can be handled by the physician. Other options for controlling the state transitions can be through, e.g., stand-alone wired or wireless joysticks/mouse, etc.

Figure 7:
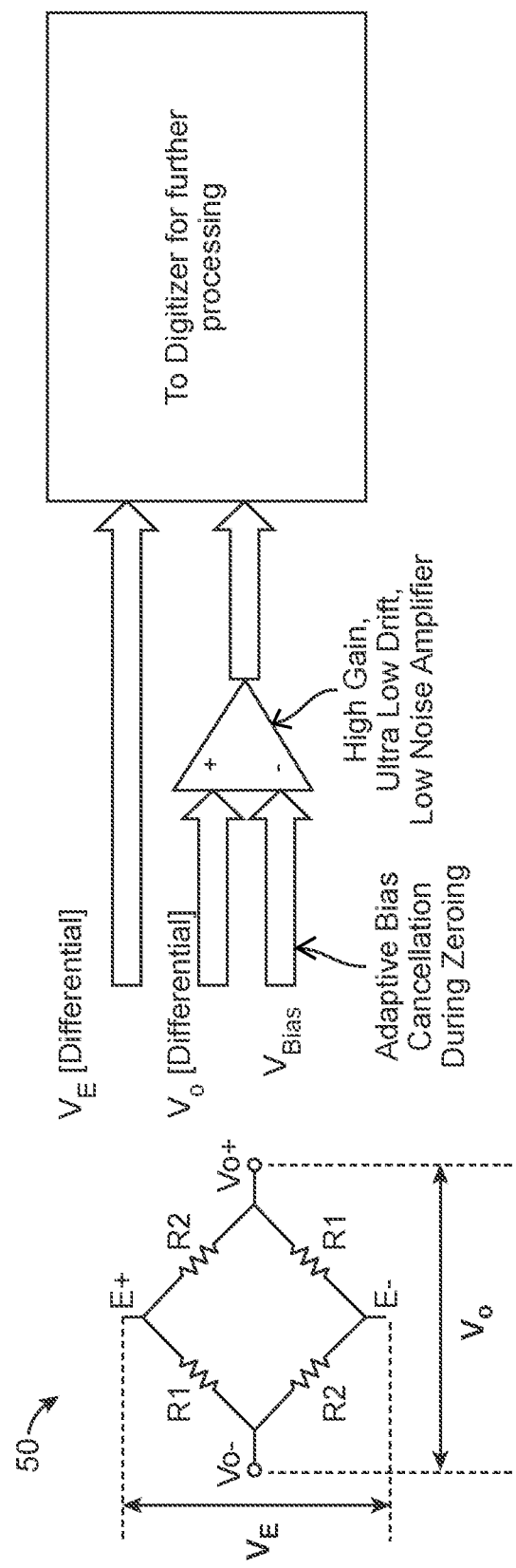
FIG. 7 shows a schematic diagram of a bias cancellation circuit as part of pre-conditioning.

As shown in schematic of FIG. 7, the electronics may accommodate a bias cancellation stage as a part of pre-conditioning. During zeroing with the sensor measuring atmospheric pressure, the average value of the signal is monitored and the same signal value is fed to a bias cancellation circuit 50 as part of the controller or processing unit 32. The resultant output, i.e., the differential between $V_E$ and the differential between $V_O$, is hence forced to zero until the time the sensor is measuring atmospheric pressure and is free from effects of local variations of atmospheric pressure as well as bias variations of the sensor. During in-vivo measurements, the output of the bias cancellation stage is the actual pressure measurement with respect to local atmospheric pressure.

Figure 8:
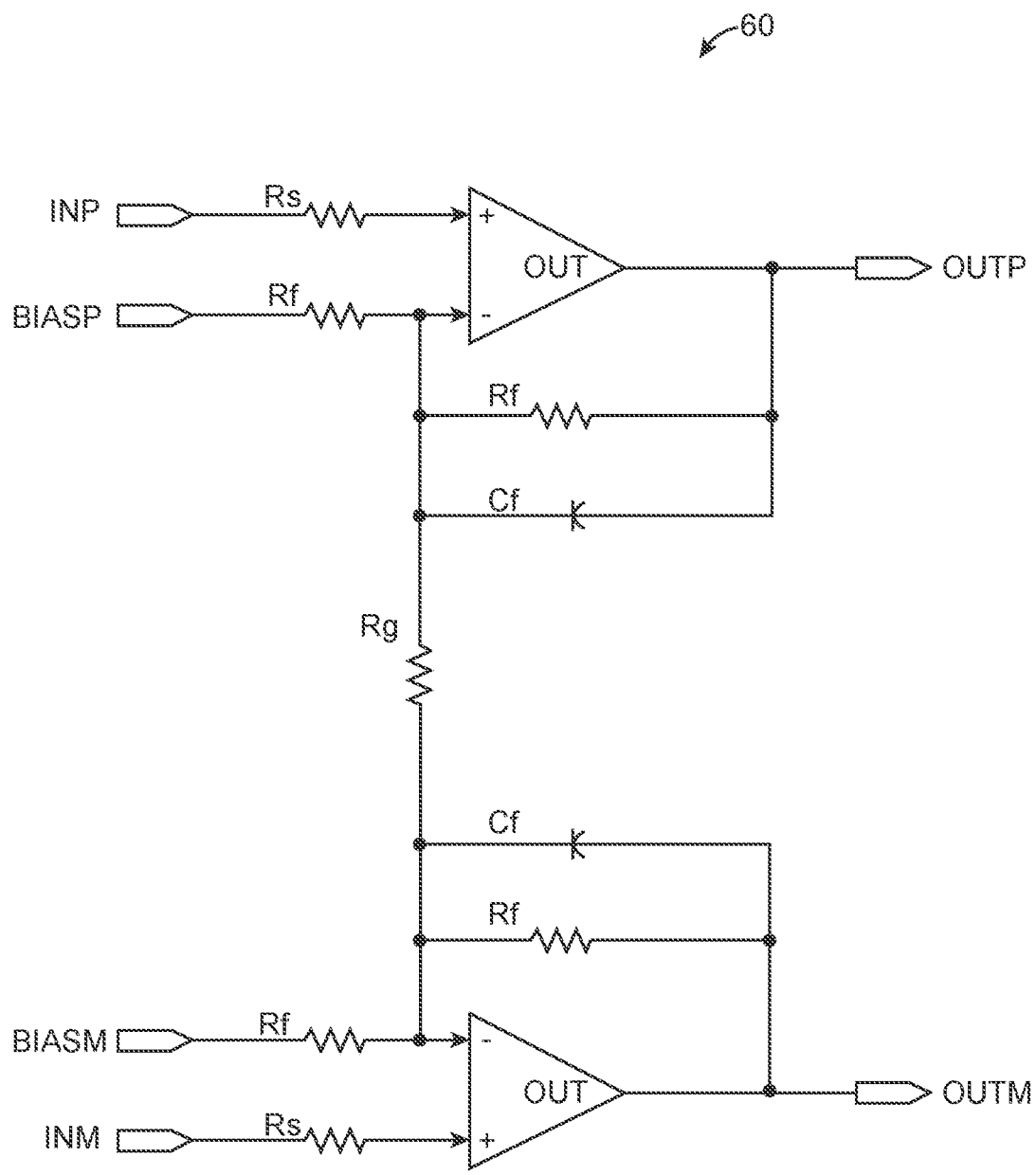
FIG. 8 shows another schematic diagram of circuit which may be used for implementation of a bias cancellation stage as part of the controller or processing unit.

FIG. 8 illustrates another circuit 60 which may be used for implementation of a bias cancellation stage as part of the controller or processing unit 32. The information about pressure is embedded in the differential voltage of INP and INM. The differential voltage comprises the incident pressure dependent voltage and fixed bias. It is extremely weak and needs large scale amplification. The amplification is achieved using instrumentation stage pre-amplifier. The bias voltage can be very significant and may be equal to several times the dynamic range of the incident pressure dependent voltage.

The cancellation of bias as a part of the pre-amplification provides the best performance in terms of dynamic range, noise figure and cost of electronics. Alternate techniques of bias cancellation done after the pre-amplification would result in inadequate gain of the front stage pre-amplifier and a separate circuit for post bias cancellation followed by yet another amplification stage to compensate for the inadequacy of the first stage. This would result in degraded noise figure and higher cost of electronics.

The user interface may be designed in the form of a state machine with a way to assist the user to navigate to the most likely next state with a click of a single button located on the connector. The button click on the connector may be wirelessly transmitted to the computing and display unit. It is intended that any of the various manufacturing and assembly processes described herein for the sensor die and/or electrode assembly may be combined in any combination as practicable. For instance, any of the assembly methods and apparatus for integrating the electrode assembly along a guidewire may be applied in combination with any of the assembly methods and apparatus for integrating the sensor along the guidewire as well. Hence, each of the variations described may be utilized alone or in any number of combinations as well.

What is claimed is:

1. A guidewire sensing device, comprising:
   a guidewire having an elongate body;
   a guidewire connector positioned at a proximal end of the elongate body;
   an aortic sensor module configured to be positioned in line with an aortic fluid lumen; and
   a processing unit located remotely from the guidewire and in wireless communication with the guidewire connector and aortic sensor module,
   wherein the aortic sensor module comprises a first pressure sensor and a second pressure sensor, the second pressure sensor being located at a different position from a position of the first pressure sensor along a length of the guidewire,
   the processing unit is configured to transmit timing information between the guidewire connector and the aortic senor module such that a sampling time of the guidewire connector and aortic sensor module is synchronized with one another, and
   the processing unit is configured to synchronize the sampling time of the guidewire connector and aortic sensor module by recording an initial local time of the processing unit and then obtaining a current time from the guidewire connector and aortic sensor module and repeating the recording of the initial local time and the obtaining of the current time for a plurality of times while introducing a random delay time during the repeating to determine a time bias relative to a local time of the processing unit.

2. The device of claim 1, wherein the guidewire connector and aortic sensor module are wirelessly in communication with one another.

3. The device of claim 1, wherein the processing unit comprises a tablet.

4. The device of claim 1, wherein the processing unit is further configured to instruct the guidewire connector and aortic sensor module to start acquiring signals simultaneously after adjusting a corresponding timing bias.

5. The device of claim 1, wherein the processing unit is in wireless communication with the guidewire connector and aortic sensor module via a low energy wireless link.

6. The device of claim 1, wherein the processing unit is further configured to adjust an acquisition of the sampling time by adding the time bias to the local time of the processing unit.

7. The device of claim 1, wherein the processing unit is further configured to equalize sampled values to account for residual post zeroing bias error due to bias drift of the guidewire connector or aortic sensor module.

8. The device of claim 1, wherein the processing unit is further configured to time shift a pressure waveform obtained from the guidewire connector and aortic sensor module to correlate with one another.

9. The device of claim 1, wherein the processing unit is further configured to specify a tolerance of respective sampling clocks of the guidewire connector and aortic sensor module to correlate any frequency mismatch between the respective sampling clocks.

10. The device of claim 1, wherein the processing unit is further configured to estimate a mean signal value of the guidewire connector and aortic sensor module when measuring atmospheric pressure.

11. A method of measuring parameters with a guidewire, comprising:
providing a guidewire having an elongate body with a guidewire connector positioned at a proximal end of the elongate body and an aortic sensor module configured to be positioned in line with an aortic fluid lumen, wherein the aortic sensor module comprises a first pressure sensor and a second pressure sensor, the second pressure sensor being located at a different position from a position of the first pressure sensor along a length of the guidewire;
wirelessly transmitting timing information between a processing unit and the guidewire connector and aortic sensor module, wherein the processing unit is located remotely from the guidewire; and
synchronizing a sampling time of the guidewire connector and aortic sensor module based on the timing information,
wherein synchronizing the sampling time comprises:
recording an initial local time of the processing unit;
obtaining a current time from the guidewire connector and aortic sensor module; and
repeating the recording of the initial local time and the obtaining of the current time for a plurality of times while introducing a random delay time during the repeating to determine a time bias relative to a local time of the processing unit.

12. The method of claim 11, wherein wirelessly transmitting comprises transmitting the timing information to a tablet.

13. The method of claim 11, wherein wirelessly transmitting comprises transmitting between the guidewire connector and aortic sensor module via a low energy wireless link.

14. The method of claim 11, wherein synchronizing a sampling time comprises determining a timing bias between the processing unit, guidewire connector, and aortic sensor.

15. The method of claim 14, further comprising adjusting a start of the sampling time between the guidewire connector and aortic sensor module based on the timing bias.

16. The method of claim 11, further comprising adjusting an acquisition of the sampling time by adding the time bias to the local time of the processing unit.

17. The method of claim 11, further comprising equalizing the sampled values to account for residual post zeroing bias error due to bias drift of the guidewire connector or aortic sensor module.

18. The method of claim 11, further comprising shifting a pressure waveform obtained from the guidewire connector and aortic sensor module to correlate with one another.

19. The method of claim 11, further comprising specifying a tolerance of respective sampling clocks of the guidewire connector and aortic sensor module to correlate any frequency mismatch between the respective sampling clocks.

20. The method of claim 11, further comprising estimating a mean signal value of the guidewire connector and aortic sensor module when measuring atmospheric pressure.

21. A guidewire sensing device, comprising:
a guidewire having an elongate body;
a guidewire connector positioned at a proximal end of the elongate body;
an aortic sensor module configured to be positioned in line with an aortic fluid lumen; and
a processing unit located remotely from the guidewire and in wireless communication with the guidewire connector and aortic sensor module,
wherein the processing unit is configured to transmit timing information between the guidewire connector and the aortic senor module such that a sampling time of the guidewire connector and aortic sensor module is synchronized with one another, and is configured to synchronize the sampling time of the guidewire connector and aortic sensor module by recording an initial local time of the processing unit and then obtaining a current time from the guidewire connector and aortic sensor module and repeating the recording of the initial local time and the obtaining of the current time for a plurality of times while introducing a random delay time during the repeating to determine a time bias relative to a local time of the processing unit.

22. A method of measuring parameters with a guidewire, comprising:
providing a guidewire having an elongate body with a guidewire connector positioned at a proximal end of the elongate body and an aortic sensor module configured to be positioned in line with an aortic fluid lumen;
wirelessly transmitting timing information between a processing unit and the guidewire connector and aortic sensor module, wherein the processing unit is located remotely from the guidewire; and
synchronizing a sampling time of the guidewire connector and aortic sensor module based on the timing information,
wherein synchronizing the sampling time comprises:
recording an initial local time of the processing unit;
obtaining a current time from the guidewire connector and aortic sensor module; and
repeating the recording of the initial local time and the obtaining of the current time for a plurality of times while introducing a random delay time during the repeating to determine a time bias relative to a local time of the processing unit.

* * * * *